(12) United States Patent
Welton et al.

(10) Patent No.: US 10,603,264 B2
(45) Date of Patent: Mar. 31, 2020

(54) SILSESQUIOXANES AND USE IN NAIL COATINGS THEREOF

(71) Applicant: Revlon Consumer Products Corporation, New York, NY (US)

(72) Inventors: Jamie Welton, Carlsbad, CA (US); Kaleb Dixon, San Diego, CA (US); Joseph Lichtenhan, Petal, MS (US); Sukhendu Hait, Hattiesburg, MS (US); Joseph Schwab, Huntington Beach, CA (US)

(73) Assignee: Revlon Consumer Products Corporation, New York, NY (US)

(*) Notice: Subject to any disclaimer, the term of this patent is extended or adjusted under 35 U.S.C. 154(b) by 0 days.

(21) Appl. No.: 16/230,724

(22) Filed: Dec. 21, 2018

(65) Prior Publication Data

US 2019/0192411 A1    Jun. 27, 2019

Related U.S. Application Data

(60) Provisional application No. 62/608,796, filed on Dec. 21, 2017.

(51) Int. Cl.

| | | |
|---|---|---|
| *A61K 8/58* | (2006.01) | |
| *A61Q 3/02* | (2006.01) | |
| *A61K 8/87* | (2006.01) | |
| *A61K 8/37* | (2006.01) | |
| *A61K 8/25* | (2006.01) | |
| *A61Q 3/00* | (2006.01) | |
| *A61K 8/891* | (2006.01) | |
| *A61K 8/81* | (2006.01) | |

(52) U.S. Cl.
CPC .............. *A61K 8/585* (2013.01); *A61K 8/25* (2013.01); *A61K 8/375* (2013.01); *A61K 8/8147* (2013.01); *A61K 8/8152* (2013.01); *A61K 8/87* (2013.01); *A61K 8/891* (2013.01); *A61Q 3/00* (2013.01); *A61Q 3/02* (2013.01)

(58) Field of Classification Search
None
See application file for complete search history.

(56) References Cited

U.S. PATENT DOCUMENTS

| | | | | |
|---|---|---|---|---|
| 9,713,585 B2* | 7/2017 | Valia | ............... | A61Q 3/02 |
| 2014/0053859 A1* | 2/2014 | Valia | ............... | A45D 29/11 |
| 2017/0056313 A1* | 3/2017 | Valia | ............... | A61K 8/37 |

FOREIGN PATENT DOCUMENTS

| | | | | |
|---|---|---|---|---|
| CN | 107118373 A | 9/2017 | | |
| WO | 2004082611 A2 | 9/2004 | | |
| WO | 2014031184 A2 | 2/2014 | | |
| WO | 2014176275 A1 | 10/2014 | | |
| WO | WO 2015061485 A1 * | 4/2015 | ............... | A61Q 3/02 |

OTHER PUBLICATIONS

Zhou, Hui et al. "Polyhedral oligomeric silsesquioxane-based hybrid materials and their applications." Materials Chemistry Frontiers, 2017, 1, 212, 19 pages.
Cordes, David B. et al. "Recent Developments in the Chemistry of Cubic Polyhedral Oligosilsesquinoxanes." Chemical Reviews, 2010, 110, 4, 93 pages.
International Search Report and Written Opinion dated Apr. 17, 2019 in connection with International Patent Application No. PCT/US2018/067340, 12 pages.

* cited by examiner

*Primary Examiner* — Brian J Davis
(74) *Attorney, Agent, or Firm* — Dorsey & Whitney LLP

(57) ABSTRACT

Polyhedral oligomeric silsesquioxanes (POSS) and formulations for nail coating are disclosed. By including a POSS in the nail coating topcoat formulation, gloss and hardness of the cured nail coating are improved without compromising removability. If included in the color layer formulation, the POSS provides improved adhesion to the nail such that a base layer is not needed. Incorporating a fatty alcohol methacrylate in the topcoat formulation also improves gloss and hardness. Polyurethane copolymers can provide the cured nail coating with good solvent removability without compromising adhesion to the nail, gloss or hardness.

18 Claims, No Drawings

SILSESQUIOXANES AND USE IN NAIL COATINGS THEREOF

CROSS-REFERENCE TO RELATED APPLICATION

This application claims the benefit of U.S. Provisional Application No. 62/608,796, filed on Dec. 21, 2017 and entitled "SILSESQUIOXANES AND USE IN NAIL COATINGS THEREOF," the entirety of which is hereby incorporated by reference for all purposes.

FIELD OF THE INVENTION

This invention relates to polyhedral oligomeric silsesquioxanes (POSS) and their use in nail coating formulations.

BACKGROUND OF THE INVENTION

Artificial fingernail and toenail formulations in the form of nail coatings and enhancements are an important product line in the appearance and beauty industry. Commercial artificial nail formulations have been used to enhance the appearance of nails and to enhance the physical properties of nails, including strengthening fragile nail surfaces.

Conventional nail coatings may be classified into two categories: nail polishes (also known as lacquers, varnish or enamels) and artificial nails (also known as gels or acrylics). Nail polishes comprise various solid components which are dissolved or suspended in non-reactive solvents. Upon application and drying, the solids deposit on the nail surface as a clear, translucent or colored film. A high degree of gloss in the cured nail polish is considered aesthetically appealing. Typically, nail polishes are easily scratched and dissolved with solvent. Such solvent solubility can be an advantage, however, as it enables the wearer to conveniently remove the nail polish.

Conventional artificial nails are comprised of chemically reactive monomers, and/or oligomers, in combination with reactive or non-reactive polymers to create systems which are typically 100% solids and do not require non-reactive solvents. Upon pre-mixing and subsequent application to the nail plate, or application and exposure to UV radiation, a chemical reaction ensues resulting in the formation of a long lasting, highly durable cross-linked thermoset nail coating that is difficult to remove. Artificial nails can possess greatly enhanced adhesion, durability, as well as scratch and solvent resistance when compared to nail polishes. However, such thermosets are much harder to remove. For acrylics and currently available "soakable gels," removal typically requires soaking in non-reactive solvents for 30-90 minutes and may also require heavily abrading the surface or scraping with a wooden or metal probe to assist the removal process. It can take more than 90 minutes of soaking (if ever) to remove traditional UV nail gels by solvent.

There is thus an on-going need to develop nail coatings that are durable with good gloss, and that are easily removed with solvent.

Nail coatings typically comprise three layers that differ in composition and are applied sequentially: a base layer that enhances adhesion between the nail and the other layers, a color layer, and a topcoat that improves durability. It would be useful, however, if the number of layers could be reduced without compromising the adhesion and durability of the nail coating as this would facilitate and expedite application.

Polyhedral oligomeric silsesquioxanes (POSS) are organosilicon compounds having a polyhedral silicate core and R groups on the surface. The general formula of a POSS may be represented by $[RSiO_{1.5}]_n$ wherein the R groups may be hydrogen or organic moieties. The R groups may be the same or different. POSS are described, for example, in Zhou et al. Mater. Chem. Front. 2017, 1, 212.

Examples of nail coating formulations are described in U.S. Pat. Nos. 8,263,677, 8,399,537, 8,901,199 and 9,717,672. U.S. Pat. No. 9,713,585 and U.S. Patent App. Pub. No. 2017/0056313 disclose the inclusion of POSS in nail coating formulations. These patents and published application are incorporated herein by reference in their entirety for all purposes within this application.

SUMMARY OF THE INVENTION

In an embodiment, this invention pertains to a compound of formula (I):

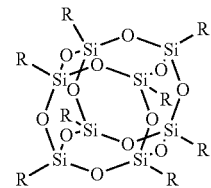

wherein at least one R group is a group comprising polyethylene glycol units and the R groups, other than the at least one R group, are alkyl groups. In an embodiment, only one R group is a group comprising polyethylene glycol units. In an embodiment, the alkyl groups have from 1 to 20 carbon atoms. In an embodiment, the alkyl groups have from 5 to 10 carbon atoms. In an embodiment, the alkyl groups have 8 carbon atoms. In an embodiment, the alkyl groups are —$CH_2CH(CH_3)CH_2C(CH_3)_3$ groups.

In an embodiment, the group comprising polyethylene glycol units has the formula —$(CH_2)_3(OCH_2CH_2)_mOCH_3$. In an embodiment, the average value of m ranges from 1 to 50. In an embodiment, the average value of m ranges from 5 to 20. In an embodiment, the average value of m ranges from 9 to 11.

In an embodiment, the compound is:

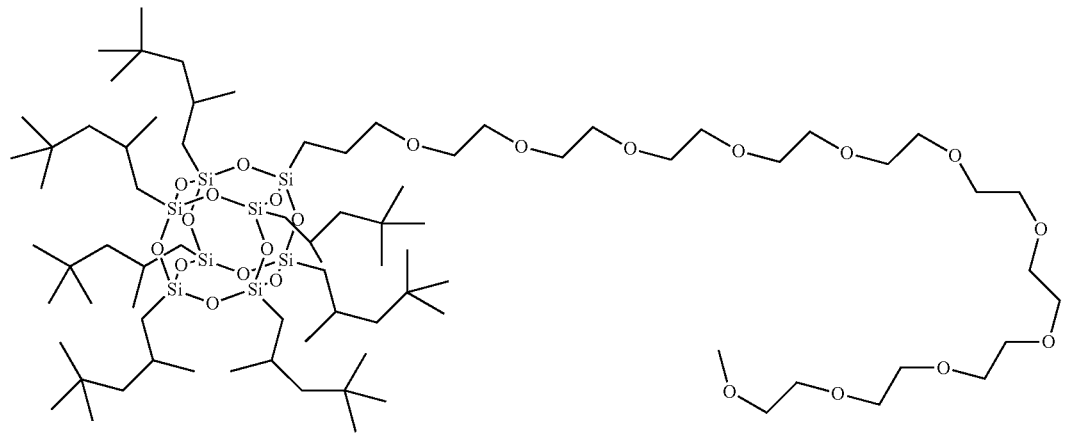

In an embodiment, this invention pertains to a nail coating formulation comprising a compound of formula (I). In an embodiment, the formulation comprises about 0.1-10 wt % of the compound of formula (I). In an embodiment, the formulation comprises about 0.1-1 wt % of the compound of formula (I). In an embodiment, the formulation comprises about 0.5 wt % of the compound of formula (I).

In an embodiment, the formulation comprises a fatty alcohol methacrylate. In an embodiment, the fatty alcohol methacrylate is stearyl methacrylate or cetyl methacrylate or a mixture thereof. In an embodiment, the formulation comprises about 0.1-10 wt % fatty alcohol methacrylate. In an embodiment, the formulation comprises about 0.5-1 wt % of fatty alcohol methacrylate.

In an embodiment, the formulation comprises a polyurethane. In an embodiment, the polyurethane is selected from the group consisting of bis-HEMA poly(1,4-butanediol)/IPDI copolymer, bis-HEMA poly(caprolactone/neopentyl glycol)/IPDI copolymer, bis-HEMA poly(caprolactone/neopentyl glycol)/1,4-butanediol/IPDI copolymer, bis-ethylhexyl poly(caprolactone neopentyl glycol)/IPDI copolymer, bis-HEMA poly(caprolactone/pentaerythritol)/IPDI copolymer, bis-ethylhexyl poly(caprolactone/pentaerythritol)/IPDI copolymer, bis-HEMA poly(caprolactone/pentaerythritol)/IPDI copolymer succinate, or bis-ethylhexyl poly(caprolactone/pentaerythritol)/IPDI copolymer succinate, and mixtures thereof.

In an embodiment, the formulation comprises trimethylolpropane trimethacrylate. In an embodiment, the formulation comprises about 0.1-10 wt % of trimethylolpropane trimethacrylate. In an embodiment, the formulation comprises about 0.1-5 wt % of trimethylolpropane trimethacrylate. In an embodiment, the formulation comprises about 3 wt % of trimethylolpropane trimethacrylate.

In an embodiment, the formulation comprises about 0.5 wt % of the compound of formula (I) and about 0.5 wt % of stearyl methacrylate.

In an embodiment, the invention pertains to a method of coating a nail comprising applying a formulation according to the invention to a nail surface. In an embodiment, the formulation is applied directly to the nail surface. In an embodiment, the formulation is applied onto a layer of another nail coating.

DETAILED DESCRIPTION

One embodiment of this invention pertains to a POSS of formula (I):

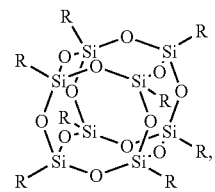

wherein at least one R group is a group comprising polyethylene glycol (PEG) units and the R groups, other than the at least one R group, are alkyl groups. The alkyl groups may be the same or different. In an embodiment, only one R group is a group comprising PEG units. In an embodiment, when R is alkyl, the alkyl group has from 1 to 20 carbon atoms. In an embodiment, when R is alkyl, the alkyl group has from 5 to 10 carbon atoms. In an embodiment, when R is alkyl, the alkyl group has 8 carbon atoms. In an embodiment, when R is alkyl, the alkyl group is —CH$_2$CH(CH$_3$)CH$_2$C(CH$_3$)$_3$.

In an embodiment, the group comprising PEG units has the formula —(CH$_2$)$_3$(OCH$_2$CH$_2$)$_m$OCH$_3$. In an embodiment, the average value of m ranges from 1 to 50. In an embodiment, the average value of m ranges from 5 to 20. In an embodiment, the average value of m ranges from 9 to 11. In an embodiment, the average value of m is 10.

In an embodiment, the POSS is:

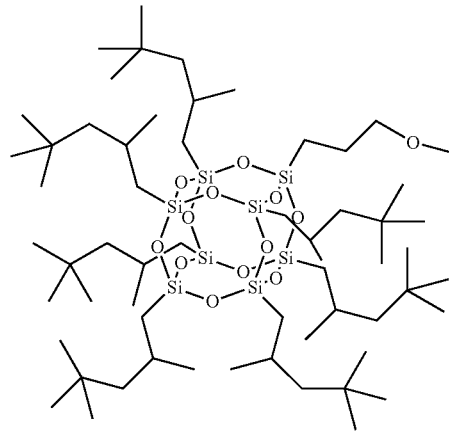
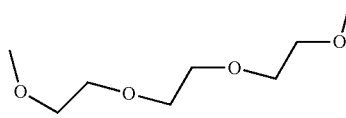

This POSS can be referred to as isooctyl/methoxy PEG-10 polysilsesquioxane.

A person having ordinary skill in the art would be able to readily make the POSS by employing general methods as described, for example, in Cordes et al. Chem. Rev. 2010, 110, 2081.

One embodiment of this invention pertains to nail coating formulations that include a POSS. The term "nail coating formulation" can refer to any formulation that is applied to a nail, for example, a topcoat formulation, a color layer formulation and/or a base layer formulation. In an embodiment, the POSS is included in both the topcoat formulation and the color layer formulation that are applied to a nail.

If present in the topcoat formulation, the POSS provides the cured nail coating with improved gloss and hardness without compromising removability. If present in the color layer formulation, the POSS provides improved adhesion of the color layer to the nail such that a base layer may not be necessary.

In an embodiment, the nail coating formulation is a topcoat formulation. In an embodiment, the amount of POSS in the topcoat formulation is about 0.1-10 wt %. In an embodiment, the amount of POSS in the topcoat formulation is about 0.1-1 wt %. Preferably, the amount of POSS in the topcoat formulation is about 0.5 wt %.

In an embodiment, the topcoat formulation comprises a fatty alcohol methacrylate. Preferably, the fatty alcohol methacrylate is stearyl methacrylate or cetyl methacrylate or a mixture thereof. In an embodiment, the amount of fatty alcohol methacrylate in the topcoat formulation is about 0.1-10 wt %. In an embodiment, the amount of fatty alcohol methacrylate in the topcoat formulation is about 0.1-1 wt %. Preferably, the amount of fatty alcohol methacrylate in the topcoat formulation is about 0.5-1 wt %.

Stearyl methacrylate can be purchased from Sigma-Aldrich Chemical Co., Milwaukee, Wis. or from Sartomer, Exton, Pa. or made according to known methods.

It has been found that stearyl methacrylate provides the cured nail coating with improved gloss and hardness (the latter resulting in better gouge and abrasion resistance) without compromising removability.

In an embodiment, the topcoat formulation comprises a polyurethane. In an embodiment, the topcoat formulation comprises bis-HEMA poly(1,4-butanediol)/IPDI copolymer, bis-HEMA poly(caprolactone/neopentyl glycol)/IPDI copolymer and/or bis-HEMA poly(caprolactone/neopentyl glycol)/1,4-butanediol/IPDI copolymer, wherein HEMA is hydroxyethylmethacrylate and IPDI is isophorone diisocyanate. Bis-HEMA poly(caprolactone/neopentyl glycol)/1,4-butanediol/IPDI copolymer may be introduced as a solution or suspension in tetrahydrofurfuryl methacrylate. These copolymers provide the cured nail coating with improved gloss and hardness and with good removability.

In an embodiment, the amount of bis-HEMA poly(1,4-butanediol)/IPDI copolymer in the topcoat formulation is about 0.1-10 wt %. In an embodiment, the amount of bis-HEMA poly(1,4-butanediol)/IPDI copolymer in the topcoat formulation is about 5-10 wt %. Preferably, the amount of bis-HEMA poly(1,4-butanediol)/IPDI copolymer in the topcoat formulation is about 6 wt %.

In an embodiment, the amount of bis-HEMA poly(caprolactone/neopentyl glycol)/IPDI copolymer in the topcoat formulation is about 1-10 wt %. In an embodiment, the amount of bis-HEMA poly(caprolactone/neopentyl glycol)/IPDI copolymer in the topcoat formulation is about 3-8 wt %. Preferably, the amount of bis-HEMA poly(caprolactone/neopentyl glycol)/IPDI copolymer in the topcoat formulation is about 5 wt %.

In an embodiment, the amount of bis-HEMA poly(caprolactone/neopentyl glycol)/1,4-butanediol/IPDI copolymer in the topcoat formulation is about 5-20 wt %. In an embodiment, the amount of bis-HEMA poly(caprolactone/neopentyl glycol)/1,4-butanediol/IPDI copolymer in the topcoat formulation is about 7-14 wt %. Preferably, the amount of bis-HEMA poly(caprolactone/neopentyl glycol)/1,4-butanediol/IPDI copolymer in the topcoat formulation is about 8 wt % or about 13 wt %.

It has been found that increasing the ratio of bis-HEMA poly(caprolactone/neopentyl glycol)/1,4-butanediol/IPDI copolymer to bis-HEMA poly(caprolactone/neopentyl glycol)/IPDI copolymer can decrease the solvent removal time without compromising gouge resistance and gloss.

Suitable polyurethane copolymers can be purchased from Dymax Corp., Torrington, Conn. or Esstech, Inc., Essington, Pa. or made according to known methods. Compared to known polyurethane copolymers having terminal methacrylated bonds, such as HEMA, and interior functional groups such as polyether or polycarbonate, the presently disclosed polyurethane copolymers may include acid- and/or hydroxyl-functionalized interior groups.

In an embodiment, the topcoat formulation comprises bis-ethylhexyl poly(caprolactone neopentyl glycol)/IPDI copolymer. This copolymer improves solvent removability. In particular, it has been found that when both bis-ethylhexyl poly(caprolactone neopentyl glycol)/IPDI copolymer and bis-HEMA poly(caprolactone/neopentyl glycol)/IPDI copolymer are present in the topcoat formulation, increasing the ratio of bis-ethylhexyl poly(caprolactone neopentyl glycol)/IPDI copolymer to bis-HEMA poly(caprolactone/neopentyl glycol)/IPDI copolymer can decrease the solvent removal time without compromising gouge resistance and gloss.

In an embodiment, the amount of bis-ethylhexyl poly(caprolactone neopentyl glycol)/IPDI copolymer in the topcoat formulation is about 5-15 wt %. Preferably, the amount of bis-ethylhexyl poly(caprolactone neopentyl glycol)/IPDI copolymer in the topcoat formulation is about 7-14 wt %. Preferably, the amount of bis-ethylhexyl poly(caprolactone neopentyl glycol)/IPDI copolymer in the topcoat formulation is about 8 wt %.

In an embodiment, the topcoat formulation comprises trimethylolpropane trimethacrylate. It has been found that the inclusion of trimethylolpropane trimethacrylate improves the feel of the cured nail coating such that it does not feel undesirably rubbery. Trimethylolpropane trimethacrylate increases crosslinking density.

In an embodiment, the amount of trimethylolpropane trimethacrylate in the topcoat formulation is about 0.1-10 wt %. In an embodiment, the amount of trimethylolpropane trimethacrylate in the topcoat formulation is about 0.1-5 wt %. Preferably, the amount of trimethylolpropane trimethacrylate in the topcoat formulation is about 3 wt %.

In an embodiment, the topcoat formulation comprises one or more solvents. Suitable solvents include butyl acetate and ethyl acetate.

In an embodiment, the nail coating formulation is a color layer formulation. In an embodiment, the color layer formulation comprises a POSS of formula (I). In an embodiment, the POSS is isooctyl/methoxy PEG-10 polysilsesquioxane.

In an embodiment, the amount of POSS in the color layer formulation is about 0.1-10 wt %. In an embodiment, the amount of POSS in the color layer formulation is about 0.1-1 wt %. Preferably, the amount of POSS in the color layer formulation is about 0.5 wt %.

In an embodiment, the color layer formulation comprises a polyurethane. In an embodiment, the color layer formulation comprises bis-HEMA poly(caprolactone/pentaerythritol)/IPDI copolymer succinate and/or bis-ethylhexyl poly(caprolactone/pentaerythritol)/IPDI copolymer. Such polyurethane copolymers may be introduced as a solution or suspension in tetrahydrofurfuryl methacrylate. These polyurethane copolymers provide improved adhesion to the nail and good solvent removability.

In an embodiment, the amount of bis-HEMA poly(caprolactone/pentaerythritol)/IPDI copolymer succinate in the color layer formulation is about 10-40 wt %. In an embodiment, the amount of bis-HEMA poly(caprolactone/pentaerythritol)/IPDI copolymer succinate in the color layer formulation is about 20-30 wt %. Preferably, the amount of bis-HEMA poly(caprolactone/pentaerythritol)/IPDI copolymer succinate in the color layer formulation is about 23 wt %.

In an embodiment, the amount of bis-ethylhexyl poly(caprolactone/pentaerythritol)/IPDI copolymer in the color layer formulation is about 0.1-10 wt %. In an embodiment, the amount of bis-ethylhexyl poly(caprolactone/pentaerythritol)/IPDI copolymer in the color layer formulation is about 4-8 wt %. Preferably, the amount of bis-ethylhexyl poly(caprolactone/pentaerythritol)/IPDI copolymer in the color layer formulation is about 6 wt %.

In an embodiment, the average molecular weight of bis-HEMA poly(caprolactone/pentaerythritol)/IPDI copolymer succinate is about 5,000 g/mol. In an embodiment, the average molecular weight of bis-ethylhexyl poly(caprolactone/pentaerythritol)/IPDI copolymer is about 5,000 g/mol.

In an embodiment, the nail coating formulation is applied directly to the nail without the need for a base layer.

The nail coating formulation can include one or more components selected from the following categories of components: reactive monomers, and/or oligomers, and/or polymers; a high-molecular weight (meth)acrylate polymer or copolymer; a polymer which conveys enhanced adhesiveness and which confers solvent sensitivity to the polymerized lattice; a urethane methacrylate resin; a (meth)acrylate monomer which provides improved adhesion, viscosity, wear and/or durability; an aromatic or aliphatic (meth)acrylate monomer which may be present to improve adhesion; a monomer and/or oligomer providing one or more free hydroxyl groups; an adhesion promoter; a non-reactive, solvent-dissolvable polymer; an optional resin; a plasticizer; a UV stabilizing agent; a polymerization initiator/photoinitiator; a polymerization regulator; a color agent; and a solvent.

Certain embodiments of the nail coating formulation may comprise an adhesion promoter in addition to POSS. The additional adhesion promoter can be selected from the group consisting of hydroxypropyl methacrylate (HPMA), hydroxyethyl methacrylate (HEMA), ethyl methacrylate (EMA), tetrahydrofurfuryl methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, methacroyloxyethyl maleate, 2-hydroxyethyl methacrylate/succinate, 1,3-glycerol dimethacrylate/succinate adduct, butyl methacrylate, isobutyl methacrylate, PEG-4 dimethacrylate, PPG monomethacrylate, trimethylolpropane trimethacrylate, isopropylidenediphenyl bisglycidyl methacrylate, lauryl methacrylate, cyclohexyl methacrylate, hexyl methacrylate, urethane methacrylate, triethylene glycol dimethacrylate, ethylene glycol dimethacrylate, tetraethylene glycol dimethacrylate, trimethylolpropane trimethacrylate, neopentylglycol dimethacylate, acetoacetoxy methacrylate, acetoacetoxyethyl methacrylate (AAEMA), polyetheramine, glycidyl methacrylates, maleic anhydride, terpolymers containing vinyl acetate, organosilanes, organotitanates, chlorinated polyolefins, sucrose acetate isobutyrate, caprylic/capric triglyceride, glyceryl hydrogenated rosinate, pentaerythryl hydrogenated rosinate, styrene/methyl styrene/indene copolymer, blocked isocyanate PVC, polyamidoamine PVC, and mixtures thereof. According to an aspect, the monomer, oligomer or polymer which provides the polymerized composition increased adhesiveness is present from about 0 to about 50 wt %.

The nail coating formulation may also include a urethane (meth)acrylate resin. While the compositions of the present embodiments can include urethane acrylates, urethane methacrylates are preferred because urethane methacrylates are less likely to cause skin sensitization than acrylate formulas. The term "urethane (meth)acrylate" as used herein means urethane methacrylate, urethane acrylate, or mixtures thereof.

These urethane oligomer (meth)acrylates are accessible, in that a polyester, polyether, polybutadiene and/or polycarbonate diol (diol component) with an aliphatic, cycloaliphatic and/or aromatic diisocyanate, for example, 1,6-hexamethylene diisocyanate (HDI), 2,4,4-trimethylhexamethylene-1,6-diisocyanate (TMDI), tetramethylene diisocyanate, isophorone diisocyanate, 4,4'-dicyclohexylmethane diisocyanate, 1,4-phenylene diisocyanate, 2,6- and 2,4-toluene diisocyanate, 1,5-naphthylene diisocyanate, 2,4'- and 4,4'-diphenylmethane diisocyanate (diisocyanate component) are reacted under amine or tin catalysis. If a molar excess of diol component compared with diisocyanate component is hereby used, terminal OH groups remain which can be esterified with an ethylenically unsaturated acid such as acrylic acid or methacrylic acid or one of their derivatives. If a molar excess of diisocyanate component compared with diol component is used, terminal isocyanate groups remain which are reacted with a hydroxyalkyl and/or hydroxyaryl (meth)acrylate and/or di(meth)acrylate and/or tri(meth)acrylate, such as, for example, 2-hydroxyethyl acrylate (HEA), 2-hydroxyethyl methacrylate (HEMA), 3-hydroxypropyl methacrylate (HPMA), 3-hydroxypropyl acrylate (HPA), glycerol dimethacrylate and/or glycerol diacrylate.

The nail coating formulation may comprise a non-reactive, solvent-dissolvable polymer. According to an aspect, the non-reactive, solvent-dissolvable polymer is a cellulose ester, nitrocellulose or sucrose benzoate. According to a particular aspect, the non-reactive, solvent-dissolvable polymer is a cellulose acetate alkylate. According to a more particular aspect, the non-reactive, solvent-dissolvable polymer is a cellulose acetate butyrate or a cellulose acetate propionate. The non-reactive, solvent-dissolvable polymer may be a mixture of any acceptable polymers. According to a further aspect, the non-reactive, solvent-dissolvable polymer may be present at from about 0 to about 75 wt %.

Certain embodiments of the nail coating formulation comprise at least one monomer which imparts to the interfacial bonds a high degree of sensitivity to organic solvent. According to an aspect, the at least one monomer may be polypropylene glycol-4-monomethacrylate (PPG-4 monomethacrylate) or polypropylene glycol-5-monomethacrylate (PPG-5 monomethacrylate). According to an aspect, suitable monomers may include any acrylated or methacrylated monomer in the polyethylene glycol (PEG), polypropylene glycol (PPG), or polybutylene glycol (PBG) families. According to an aspect, such monomers are present at from about 0 to about 70 wt %.

In certain embodiments, the monomer that imparts to the interfacial bonds a high degree of sensitivity to organic solvent may be a polyol modified urethane (meth)acrylate.

In certain embodiments, the nail coating formulation further comprises monomers and oligomers chosen such that various bonds within the resulting thermoset are provided an increased sensitivity to solvent. In certain embodiments, such monomers and oligomers are selected from the group consisting of propoxylated allyl methacrylate, methoxy polyethylene glycol (350) monomethacrylate, polyethylene glycol (600) monomethacrylate, stearyl methacrylate, tridecyl methacrylate, hydroxyethyl methacrylate acetate, and mixtures thereof.

Certain embodiments of the nail coating formulation may comprise a urethane (meth)acrylate resin which may convey flexibility and toughness to the polymerized product. In certain embodiments, urethane methacrylates are preferred. The urethane (meth)acrylate oligomer may be present from about 0 to about 80 wt %. In certain embodiments, the urethane (meth)acrylate may have a molecular weight (grams/mole) of from about 100 to about 20,000. In certain embodiments, the urethane (meth)acrylate may have a molecular weight of from about 300 to about 15,000. In certain embodiments, the urethane (meth)acrylate may have a molecular weight of from about 500 to about 13,000. In certain embodiments, the urethane (meth)acrylate may have a molecular weight of from about 500 to about 6,000.

Certain embodiments of the present disclosure may comprise other aromatic or aliphatic (meth)acrylate monomers which may be present to improve adhesion. The (meth)acrylate monomer may be a pyromellitic dianhydride glyceryl dimethacrylate (PMGDM), pyromellitic dianhydride glyceryl dimethacrylate (PMDM) or 4-methacryloyloxylethyl trimellitate anhydride (4-META). In general, this methacrylate monomer may be an acid-functional, (meth)acrylate monomer. The acid-functional, (meth)acrylate monomer may be a carboxylic acid polymer. This (meth)acrylate monomer may be present from about 0 to about 70 wt %.

The nail coating formulation may comprise monomers and oligomers having a plurality of free hydroxyl groups. The hydroxyl groups of the nail coating formulation may be available to form hydrogen bonds with a substrate which may be a keratinous nail surface. The hydroxyl groups of the nail coating formulation may be available to form hydrogen bonds with a substrate which may be a surface of a natural nail or artificial nail enhancement coating.

The nail coating formulation may contain from about 0.001 wt % to about 20 wt % of a plasticizer. The compositions of the invention may contain from about 0.01 wt % to about 15 wt %, from about 0.05 wt % to about 10 wt %, from about 0.1 wt % to about 5 wt %, or from about 0.5 wt % to about 2 wt % of a plasticizer. The plasticizer causes the polymerized nail structure to have improved flexibility and reduced brittleness. Suitable plasticizers may be esters, low volatility solvents, or non-ionic materials such as nonionic organic surfactants or silicones. In certain embodiments, the nail coating formulation further comprises from about 0.001 wt % to about 20 wt %, from about 0.01 wt % to about 15 wt %, from about 0.05 wt % to about 10 wt %, from about 0.1 wt % to about 5 wt %, or from about 0.5 wt % to about 2 wt % of a plasticizer selected from the group consisting of esters, low volatility solvents (paraffinic hydrocarbons, butyrolactone, xylene, methyl isobutyl ketone), non-ionic surfactants, non-ionic silicones, isostearyl isononanoate, silicones, diisobutyl adipate, trimethyl pentanyl diisobutyrate, acetyl tributyl citrate, and mixtures thereof.

The nail coating formulation may be polymerizable with actinic radiation. The actinic radiation may be visible, ultraviolet (UV), or electron beam radiation. The UV radiation may be characterized by a wavelength, or group of wavelengths, typically, but not limited to about 320 to about 420 nanometers.

After the nail coating formulation is applied, it is polymerized or cured. The nail coating formulation comprises ethylenically unsaturated (meth)acrylates which may be polymerized or cured by a UV-initiated, free-radical polymerization method. Persons of ordinary skill in the polymerization arts may readily determine suitable photoinitiators for use with the invention. Suitable photoinitiators include, but are not limited to, benzoyldiphenylsphosphinates, phenyl ketones, and dimethyl ketals. A suitable photoinitiator is a 2,4,6-trimethylbenzoyldiphenylphosphorous derivative. A suitable derivative is ethyl-2,4,6-trimethylbenzoyldiphenylphosphinate, which may be obtained under the trade name Lucirin® TPO-L (BASF Aktiengesellschaft, Ludwigshafen, DE). Another non-limiting suitable derivative is 2,4,6-trimethylbenzoyldiphenylphosphine oxide, which may be obtained under the trade name Lucerin® TPO (BASF) or as Genocure® TPO (Rahn Aktiengesellschaft, Zurich, Switzerland). The 2,4,6-trimethylbenzoyldiphenylphosphinate photoinitiator may be present from about 0% to about 20 wt %. A preferred photoinitiator is Irgacure 819 (BASF).

The color layer formulation may comprise up to 20 wt % pigments and/or dyes. The topcoat formulation may have up to 1 wt % pigments and/or dyes. High concentrations of pigments and/or dyes may absorb UV radiation. To compensate therefor, certain embodiments of the present disclosure may comprise higher concentrations, up to 20 wt % photoinitiator.

The nail coating formulation may comprise at least one non-reactive solvent. A suitable non-reactive solvent is readily volatile at room temperature and is a good solvent for the remaining ingredients. Upon application, the non-reactive solvent readily volatilizes leaving regions of increased porosity throughout the nail coating. These porous regions later facilitate the entry of a remover solvent which may be acetone.

Suitable non-reactive solvents may be selected from the group consisting of ketones, alkyl acetates, alcohols, alkanes, alkenes, and mixtures thereof. Suitable solvents may be selected from the group consisting of acetone, ethyl acetate, butyl acetate, isopropyl alcohol, ethanol, methyl ethyl ketone, toluene, hexane, and mixtures thereof. A particularly suitable solvent is acetone. Typically a solvent or a mixture of solvents is included at up to about 70 wt %.

In an embodiment, the invention pertains to a method of coating a nail comprising applying a formulation according to the invention to a nail surface. In an embodiment, the formulation is applied directly to the nail surface. In an embodiment, the formulation is applied onto a layer of another nail coating.

EXAMPLES

Experiments were performed to determine the effects of various substances on the properties of the nail coatings.

For the topcoat, the properties studied were gloss, abrasion resistance, gouge resistance and solvent removability. It is desirable for a topcoat to have high gloss (resulting in a pleasing aesthetic appearance), good abrasion resistance and gouge resistance (which indicates good durability after application), and easy solvent removability (so that a wearer may easily remove the nail coating, if desired).

For the color layer, dry and wet adhesion to the nail were studied. High adhesion is desirable so that the nail coating remains attached to the nail during wear.

Example 1—Comparison of the Effect of POSS and Stearyl Methacrylate on Topcoat Gouge Resistance Test formulations were prepared by separately adding each of the additives listed in Table 1 to samples of Shellac Xpress5™ topcoat formulation (Creative Nail Design, Inc., Vista, Calif.). The gouge scores in Table 1 reflect an average of three repeat experiments (hence fractional scores are possible).

TABLE 1

| Additive | 0 MIN | 30 MIN | 60 MIN | 120 MIN |
|---|---|---|---|---|
| Aminoethylaminopropylisobutyl POSS | 0.00 | 1.33 | 5.33 | 6.67 |
| AminopropylIsobutyl POSS | 0.00 | 1.33 | 7.33 | 7.33 |
| N-Phenylaminopropyl POSS in 30% Butyl Acetate | 0.00 | 3.67 | 7.67 | 9.33 |
| N-Methylaminopropylisobutyl POSS | 0.00 | 4.00 | 6.67 | 7.67 |
| Aminopropylisooctyl POSS | 0.00 | 4.00 | 6.00 | 7.00 |
| Polyether-modified, hydroxy-functional polydimethylsiloxane | 0.00 | 0.00 | 0.00 | 0.00 |
| Control (no additive) | 0.00 | 1.67 | 5.67 | 6.67 |
| Stearyl methacrylate | 0.00 | 6.67 | 7.00 | 10.00 |
| Isooctyl/methoxy PEG-10 polysilsesquioxane (POSS) | 0.00 | 4.00 | 6.00 | 9.67 |

All POSS were obtained from Hybrid Plastics, Hattiesburg, MS. Stearyl methacrylate was obtained from Sigma-Aldrich Chemical Co., Milwaukee, WI. Polyether-modified, hydroxy-functional polydimethylsiloxane was obtained from Byk USA Inc, Wallingford, CT.
Pencils used for scoring: 9H (score 19), 8H (score 18), 7H (score 17), 6H (score 16), 5H (score 15), 4H (score 14), 3H (score 13), 2H (score 12), H (score 11), F (score 10), HB (score 9), B (score 8), 2B (score 7), 3B (score 6), 4B (score 5), 5B (score 4), 6B (score 3), 7B (score 2), 8B (score 1), 9B (score 0).

The above gouge resistances were measured according to the below protocol.

1. Clean glass micro slides (75×50 mm) with acetone. Weigh slides initial weight.
2. Pour out enough of the sample on to the top of the slide to ensure full coverage during draw down (approximately 3 mL). Use a 2"×2" draw down bar to obtain a 10 mil film casting over the slides.
3. Cure for 1 min under LED lamp.
4. After cure, immediately take the softest pencil (9B) and at ~30° angle move the pencil in an upward motion. Use sanding sheets to ensure that each pencil tip is flat prior to gouging. Increase the pencil strength until a full gouge appears with minimal effort. Proper gouging of a film will happen when the pencil easily penetrates though to the micro slide surface.
5. Repeat the gouging at the indicated times.

All tests were performed in triplicate. The data showed that stearyl methacrylate and isooctyl/methoxy PEG-10 polysilsesquioxane provide higher gouge resistance at the 120 minute time point than the control composition or the other POSS tested.

Example 2—Effect of Additives on Topcoat Formulation Properties

Topcoat formulations were prepared as defined in Table 2 in order to study the effect of various additives on the gloss, abrasion resistance, gouge resistance and solvent removability of the topcoat. All quantities are expressed as wt %.

TABLE 2

| Materials | I-2 | I-3 | L-2 | L-3 | M-2 | M-3 | I | L | M |
|---|---|---|---|---|---|---|---|---|---|
| Tetrahydrofurfuryl methacrylate | 19.29 | 19.01 | 19.29 | 19.01 | 19.29 | 19.01 | 19.01 | 19.01 | 19.01 |

TABLE 2-continued

| Materials | I-2 | I-3 | L-2 | L-3 | M-2 | M-3 | I | L | M |
|---|---|---|---|---|---|---|---|---|---|
| Cellulose acetate butyrate | 21.88 | 21.66 | 21.88 | 21.66 | 21.88 | 21.66 | 21.66 | 21.66 | 21.66 |
| Isobornyl methacrylate | 1 | 1 | 1 | 1 | 1 | 1 | 1 | 1 | 1 |
| Butyl acetate | 7.88 | 7.81 | 7.88 | 7.81 | 7.88 | 7.81 | 7.81 | 7.81 | 7.81 |
| Ethyl acetate | 9.37 | 9.28 | 9.37 | 9.28 | 9.37 | 9.28 | 9.28 | 9.28 | 9.28 |
| Bis-HEMA poly(1,4-butanediol)/IPDI copolymer | 5.99 | 5.94 | 5.99 | 5.94 | 5.99 | 5.94 | 5.94 | 5.94 | 5.94 |
| Bis-HEMA poly(caprolactone/neopentyl glycol)/IPDI copolymer | 4.85 | 4.85 | 0 | 0 | 0 | 0 | 4.85 | 0 | 0 |
| Bis-ethylhexyl poly(caprolactone neopentyl glycol)/IPDI copolymer | 8.12 | 8.04 | 8.12 | 8.04 | 12.97 | 12.89 | 8.04 | 8.04 | 12.89 |
| Bis-HEMA poly(caprolactone/neopentyl glycol)/1,4-butanediol/IPDI copolymer | 8.05 | 7.97 | 12.9 | 12.82 | 8.05 | 7.97 | 7.97 | 12.82 | 7.97 |
| Isooctyl/methoxy PEG-10 polysilsesquioxane (POSS) | 0.51 | 0.51 | 0.51 | 0.51 | 0.51 | 0.51 | 0.51 | 0.51 | 0.51 |
| Stearyl methacrylate | 0.51 | 0.51 | 0.51 | 0.51 | 0.51 | 0.51 | 0.51 | 0.51 | 0.51 |
| Trimethylolpropane trimethacrylate | 0 | 0 | 0 | 0 | 0 | 0 | 2.95 | 2.95 | 2.95 |
| Trifunctional urethane trimethacrylate | 2 | 2.95 | 2 | 2.95 | 2 | 2.95 | 0 | 0 | 0 |
| 5% Irg 819/EtAc | 7.85 | 7.77 | 7.85 | 7.77 | 7.85 | 7.77 | 7.77 | 7.77 | 7.77 |
| 10% Butylated hydroxytoluene/BuAc | 0.5 | 0.5 | 0.5 | 0.5 | 0.5 | 0.5 | 0.5 | 0.5 | 0.5 |
| Ethyl (2,4,6-trimethylbenzoyl) phenylphosphinate | 1.5 | 1.5 | 1.5 | 1.5 | 1.5 | 1.5 | 1.5 | 1.5 | 1.5 |
| 0.1% external violet 2 dye in hydroxypropyl-methacrylate | 0.7 | 0.7 | 0.7 | 0.7 | 0.7 | 0.7 | 0.7 | 0.7 | 0.7 |

These samples were tested according to the below protocols. Each test was performed in triplicate. The results are shown in Table 3. The control formulation is Shellac Xpress5® topcoat, which had the following formulation in this Example:

| Component | Wt % |
|---|---|
| Bis-HEMA poly(1,4-butanediol)/IPDI copolymer | 18.172 |
| Bis-HEMA poly(aprolactone/neopentyl/glycol)/IPDI copolymer | 8.391 |
| Tetrahydrofurfuryl methacrylate | 20.712 |
| 10% Butylated hydroxytoluene in BuAc | 0.500 |
| Trimethylolpropane trimethacrylate | 1.040 |
| Isobornyl methacrylate | 1.030 |
| n-Butyl Acetate | 8.041 |
| Ethyl Acetate | 9.562 |
| Cellulose acetate butyrate | 22.312 |
| Ethyl (2,4,6-trimethylbenzoyl) phenylphosphinate | 1.540 |
| 5% Irg 819 in EtAc | 8.000 |
| 0.1% external violet 2 dye in hydroxypropylmethacrylate | 0.700 |
| Total | 100.000 |

Double Rub Removal Test
1. Clean glass micro slides (75×50 mm) with acetone. Weigh slides initial weight.
2. Pour out enough of the sample on to the top of the slide to ensure full coverage during draw down (approximately 3 mL). Use a 2"×2" draw down bar to obtain a 10 mil film casting over the slides.
3. Cure for 1 min under LED lamp.
4. After cure, postcure all samples in a QUV light chamber for 2 hours.
5. Weigh slide to obtain film weight.
6. Saturate cosmetic pad (Graham "Hands Down") with acetone. Place saturated pad on the center of cured film and begin counting double rubs. One double run is equal to wiping in and upward AND downward direction.
7. Count the amount of double rubs required to remove the film from the slide. Some films will rapidly detach from the micro slide surface, some will dissolve completely, and others will dissolve in a very small area (called a rip).

The lower the number of rubs, the better the solvent removability. The data was also normalized to take into account the variation in thickness of the films formed by different formulations.

Initial Gloss Test
1. Position a Q-Panel (Q-Lab, Westlake, Ohio) test substrate over the middle, bottom edge of a Leneta card (Leneta Co., Mahwah, N.J.) and ensure the hole (i.e., the "Q") is resting on the black side of the Leneta card. This Q represents the top portion of the Q-Panel. Trace inside the Q and around the Q-Panel with a permanent marker while keeping it steady over the white side of the card. Remove Q-Panel. Then, take the rectangle template and align to the Q-Panel on the Leneta card. Trace a rectangle in the middle of this Q-Panel.
2. Place the Leneta card on a vacuum plate. Set the applicator on top of the Q-Panel and above the rectangle such that the sample film covers the entire rectangle as it is drawn down the Leneta card.
3. Apply about 3 mL of sample in front of the applicator. Then, draw the applicator smoothly down the length of the Leneta card. Cut around the Q-panel Leneta card and carefully place on the drying rack to rest.
4. After 5 minutes resting time, place the sample card into an LED lamp, with the white side of the card entering the lamp first. Align the 'Q,' marked in the middle of the card, to the center of the LED insert.
5. Remove card after curing is completed. Place fan facing towards the LED lights at least 1.5 mins to help cool down. Place cured sample film in the drying rack and allow it to age for the specified amount of time (e.g., 1 hour, 24 hours or 3 days).
6. After aging has been completed, fully saturate a cosmetic pad with IPA and fully remove the inhibition layer. Allow the solvent to fully dry and place back in drying rack.
7. At the specified time place a BYK Tri Gloss-meter (Byk USA Inc, Wallingford, Conn.) directly over the rectangle, ensuring the meter is centered directly over the sample. Record the gloss reading at angles of 20/60/85 degrees.

The higher the score in this test, the better the gloss.
Sand Abrasion Test

Abrade samples according to ASTM D968-17 and measure gloss per the initial gloss test (above). The higher the score in this test, the greater the abrasion resistance.
Gouge Resistance Test The gouge resistance of the cured nail coating was measured with pencils of varying hardness (as in Example 1). The scores indicate the softest pencil that was able to gouge the nail coating. The harder the pencil, the better the gouge resistance.

Example 3—Effect of Trimethylolpropane Trimethacrylate in the Topcoat

Referring to Table 2, formulations I, L and M include trimethylolpropane trimethacrylate while the comparative formulations do not.

It was found that addition of trimethylolpropane trimethacrylate to the topcoat formulation improves the feel of the cured topcoat such that it does not feel undesirably rubbery. The data in Table 3 showed that trimethylolpropane trimethacrylate does not compromise, gloss, abrasion resistance or gouge resistance relative to the comparative formulations.

Example 4—Comparison of Copolymers in the Topcoat

Referring again to Table 2, formulations I and L differ in the amounts of bis-HEMA poly(caprolactone/neopentyl glycol)/1,4-butanediol/IPDI copolymer and bis-HEMA poly(caprolactone/neopentyl glycol)/IPDI copolymer.

The data in Table 3 showed that increasing the amount of bis-HEMA poly(caprolactone/neopentyl glycol)/1,4-butanediol/IPDI copolymer and decreasing the amount bis-HEMA poly(caprolactone/neopentyl glycol)/IPDI copolymer in going from formulation I to formulation L decreased the solvent removal time. Furthermore, initial gloss and gloss after sand abrasion were not compromised.

Example 5—Comparison of Copolymers in the Topcoat

Referring again to Table 2, formulations I and M differ in the amounts of bis-HEMA poly(caprolactone/neopentyl glycol)/IPDI copolymer and bis-ethylhexyl poly(caprolactone neopentyl glycol)/IPDI copolymer.

The data in Table 3 showed that increasing the amount of bis-ethylhexyl poly(caprolactone neopentyl glycol)/IPDI copolymer and decreasing the amount of bis-HEMA poly(caprolactone/neopentyl glycol)/IPDI copolymer in going from formulation I to formulation M decreased the solvent removal time. Furthermore, gloss after sand abrasion was not compromised.

Example 6—Color Layer Adhesion Testing

Color layer formulations were prepared as defined in Table 4 in order to study the effects of various copolymers on the adhesion of the color layer. All quantities are expressed as wt %.

TABLE 3

| Results | I-2 | I-3 | L-2 | L-3 | M-2 | M-3 | I | L | M | Control |
|---|---|---|---|---|---|---|---|---|---|---|
| Double Rub Removal | 35 | 26 | 19 | 32 | 11 | 12 | 69 | 41 | 22 | 80 |
| Removal Normalized by weight of film | 84 | 94 | 65 | 87 | 33 | 47 | 214 | 127 | 72 | 245 |
| Double rub normalized by control | 34% | 38% | 27% | 36% | 14% | 19% | 85% | 52% | 29% | 100% |
| Initial Gloss 20 deg | 75.15 | 77.7 | 75.8 | 78.8 | 68 | 71.5 | 77 | 77 | 74.7 | 77.6 |
| Initial Gloss 60 deg | 87.5 | 87.4 | 86.2 | 87.4 | 86.5 | 86.4 | 87 | 86.6 | 85.9 | 86.9 |
| 20 deg Sand Abrasion 1 hr |  |  |  |  |  |  | 4.1 | 7.9 | 3.8 | 3 |
| 60 deg Sand Abrasion 1 hr |  |  |  |  |  |  | 26.5 | 35.8 | 24.8 | 23 |
| 20 deg Sand Abrasion 3 day |  |  |  |  |  |  | 3.9 | 3.3 | 3.5 | 6.6 |
| 60 deg Sand Abrasion 3 day |  |  |  |  |  |  | 26.9 | 30 | 25.2 | 32.1 |
| Gouge 1 hr | 9B | 9B | 8B | 6B | 4.3B | 6.7B | 5B | 6B | 5B | 3B |
| Gouge 24 hour | 4.3B | 4B | 3.7B | B-HB | B | 2B | 2H | F | 1.5B | 3H |

TABLE 4

| | Control | A | B | C | D | E |
|---|---|---|---|---|---|---|
| Materials | | | | | | |
| Tetrahydrofurfuryl methacrylate | 20.78 | 12.51 | 12.51 | 4.24 | 4.24 | 4.24 |
| Polypropyleneglycol (5) methacrylate | 26.31 | 26.31 | 26.31 | 26.31 | 26.31 | 26.31 |
| 0.1% external violet 2 dye in hydroxypropylmethacrylate | 0.70 | 0.70 | 0.70 | 0.70 | 0.70 | 0.70 |
| Bis-HEMA poly(caprolactone/neopentyl glycol)/IPDI copolymer | 15.53 | 0 | 0 | 0 | 0 | 0 |
| Bis-HEMA poly(caprolactone/pentaerythritol)/IPDI copolymer | 0 | 0 | 0 | 7.765 | 15.53 | 7.765 |
| Bis-HEMA poly(caprolactone/pentaerythritol)/IPDI copolymer succinate | 0 | 15.53 | 15.53 | 7.765 | 0 | 7.765 |
| Bis-ethylhexyl poly(caprolactone/pentaerythritol)/IPDI copolymer | 0 | 4.94 | 0 | 9.88 | 4.94 | 4.94 |
| Bis-ethylhexyl poly(caprolactone/pentaerythritol)/IPDI copolymer Succinate | 0 | 0 | 4.94 | 0 | 4.94 | 4.94 |
| Cellulose acetate butyrate | 20.91 | 20.91 | 20.91 | 20.91 | 20.91 | 20.91 |
| Acetone | 8.19 | 8.19 | 8.19 | 8.19 | 8.19 | 8.19 |
| Ethyl acetate | 6.38 | 6.38 | 6.38 | 6.38 | 6.38 | 6.38 |
| Irgacure 819 | 0.50 | 0.50 | 0.50 | 0.50 | 0.50 | 0.50 |
| Diphenyl(2,4,6-trimethylbenzoyl)phosphine oxide | 0.60 | 0.60 | 0.60 | 0.60 | 0.60 | 0.60 |
| Butylated hydroxytoluene | 0.10 | 0.10 | 0.10 | 0.10 | 0.10 | 0.10 |
| Dry Adhesion Test | | | | | | |
| Adhesion squares removed after tape pull | 23.5 | 16 | 19 | 6.75 | 18.5 | 9.5 |

The adhesion of color layer samples was tested according to the following protocols.

Dry Adhesion Test
1. Follow ASTM D3359 for Cross Hatch Adhesion, using the appropriate scoring tool, and adhesion method tape. Thoroughly cross-score a sample of formulation applied to a simulated nail substrate. Brush away excess material.
2. Press tape firmly over the scored portion, and remove the tape firmly.
3. Count the number of squares removed from the scored grid. This is the dry adhesion ranking, 0 squares removed is perfect adhesion.

Wet Adhesion Test
1. Fill a shallow Pyrex dish with tap water at 25° C. Fully submerge completed dry adhesion panels, face up, for 15 minutes.
2. Remove panels, and gently blot dry with paper towels. The simulated nail substrate is now fragile and easily deformed, and must be allowed to fully dry before proceeding (at least 3-24 hours drying time). Taping the sheets to Q-Panels allows them to recover without excessive deformation.
3. Apply new adhesion tape over the scored portion, press firmly, and firmly remove tape again. Count the number of additional squares removed from the scored grid. This is the wet adhesion ranking.

Each test was performed in triplicate.

The lower the score in the dry or wet adhesion test, the better the adhesion.

The data in Table 4 showed that decreasing the amount of bis-HEMA poly(caprolactone/neopentyl glycol)/IPDI copolymer and increasing the amount of bis-HEMA poly(caprolactone/pentaerythritol)/IPDI copolymer succinate and/or bis-ethylhexyl poly(caprolactone/pentaerythritol)/IPDI copolymer improved the dry adhesion of the color layer.

Color layer formulations with and without a pigment were next prepared as defined in Table 5 and their dry adhesion tested according to above protocol. Samples that contain the color concentrate were prepared from 80 wt % base formulation (as indicated) and 20 wt % Banana Clips color formulation (Creative Nail Design, Inc., Vista, Calif.). All quantities in Table 5 are expressed as wt % before addition of color concentrate, if any.

TABLE 5

| | U | V | X | Y | Z |
|---|---|---|---|---|---|
| Materials | | | | | |
| Polypropyleneglycol (5) methacrylate | 26.31 | 26.31 | 26.31 | 26.31 | 26.31 |
| Cellulose acetate butyrate | 20.91 | 20.91 | 20.91 | 20.91 | 20.91 |
| Tetrahydrofurfuryl methacrylate | 20.78 | 2.97 | 7.06 | 7.06 | 0 |
| Bis-HEMA poly(caprolactone/neopentyl glycol)/IPDI copolymer | 15.53 | 7.765 | 0 | 0 | 0 |
| Bis-HEMA poly(caprolactone/pentaerythritol)/IPDI copolymer | 0 | 0 | 0 | 0 | 11.095 |

TABLE 5-continued

| | U | V | X | Y | Z |
|---|---|---|---|---|---|
| Bis-HEMA poly(caprolactone/pentaerythritol)/IPDI copolymer succinate | 0 | 11.095 | 22.19 | 22.19 | 11.095 |
| Bis-ethylhexyl poly(caprolactone/pentaerythritol)/IPDI copolymer | 0 | 0 | 7.06 | 0 | 14.12 |
| Bis-ethylhexyl poly(caprolactone/pentaerythritol)/IPDI copolymer cuccinate | 0 | 14.48 | 0 | 7.06 | 0 |
| Butyl acetate | 14.57 | 14.57 | 14.57 | 14.57 | 14.57 |
| Butylated hydroxytoluene | 0.1 | 0.1 | 0.1 | 0.1 | 0.1 |
| 0.1% external violet 2 dye in hydroxypropylmethacrylate | 0.7 | 0.7 | 0.7 | 0.7 | 0.7 |
| Irgacure 819 | 0.5 | 0.5 | 0.5 | 0.5 | 0.5 |
| Diphenyl(2,4,6-trimethylbenzoyl)phosphine oxide | 0.6 | 0.6 | 0.6 | 0.6 | 0.6 |
| Dry Adhesion Test | | | | | |
| Adhesion squares removed after tape pull (no color concentrate) | 0.75 | 1 | 0.25 | 0.5 | 2.5 |
| Adhesion squares removed after tape pull (20% color concentrate added) | 33 | 0.5 | 12.75 | 3 | 7.5 |

The data in Table 5 showed that the effects of decreasing the amount of bis-HEMA poly(caprolactone/neopentyl glycol)/IPDI copolymer and increasing the amount of bis-HEMA poly(caprolactone/pentaerythritol)/IPDI copolymer succinate and/or bis-ethylhexyl poly(caprolactone/pentaerythritol)/IPDI copolymer upon dry adhesion were increased by the presence of color concentrate.

Color layer formulations comprising a pigment as defined in Table 6 were then tested in the wet and dry adhesion tests. All quantities are expressed as wt %.

TABLE 6

| | P | Q | V | X | Y | Z |
|---|---|---|---|---|---|---|
| Materials | | | | | | |
| Polypropyleneglycol (5) methacrylate | 26.31 | 26.31 | 26.31 | 26.31 | 26.31 | 26.31 |
| Cellulose acetate butyrate | 20.91 | 20.91 | 20.91 | 20.91 | 20.91 | 20.91 |
| Tetrahydrofurfuryl methacrylate | 2.97 | 2.97 | 2.97 | 7.06 | 7.06 | 0 |
| Bis-HEMA poly(caprolactone/neopentyl glycol)/IPDI copolymer | 7.765 | 7.765 | 7.765 | 0 | 0 | 0 |
| Bis-HEMA poly(caprolactone/pentaerythritol)/IPDI copolymer | 0 | 11.095 | 0 | 0 | 0 | 11.095 |
| Bis-HEMA poly(caprolactone/pentaerythritol)/IPDI copolymer succinate | 11.095 | 0 | 11.095 | 22.19 | 22.19 | 11.095 |
| Bis-ethylhexyl poly(caprolactone/pentaerythritol)/IPDI copolymer | 14.48 | 0 | 0 | 7.06 | 0 | 14.12 |
| Bis-ethylhexyl poly(caprolactone/pentaerythritol)/IPDI copolymer succinate | 0 | 14.48 | 14.48 | 0 | 7.06 | 0 |
| Butyl acetate | 14.57 | 14.57 | 14.57 | 14.57 | 14.57 | 14.57 |
| Butylated hydroxytoluene | 0.1 | 0.1 | 0.1 | 0.1 | 0.1 | 0.1 |
| 0.1% external violet 2 dye in hydroxypropylmethacrylate | 0.7 | 0.7 | 0.7 | 0.7 | 0.7 | 0.7 |
| Irgacure 819 | 0.5 | 0.5 | 0.5 | 0.5 | 0.5 | 0.5 |
| Butyl acetate | 14.57 | 14.57 | 14.57 | 14.57 | 14.57 | 14.57 |
| Dry Adhesion Test | | | | | | |
| Adhesion squares removed after tape pull (no color concentrate) | 4 | 2 | 3 | 3 | 7 | 9 |
| Wet Adhesion Test | | | | | | |
| Adhesion squares removed after tape pull (20% color concentrate added) | 49 | 37.5 | 36 | 18 | 28 | 22 |

The data in Table 6 showed that decreasing the amount of bis-HEMA poly(caprolactone/neopentyl glycol)/IPDI copolymer and increasing the amount of bis-HEMA poly(caprolactone/pentaerythritol)/IPDI copolymer succinate and/or bis-ethylhexyl poly(caprolactone/pentaerythritol)/IPDI copolymer increased adhesion in the wet adhesion test.

Example 7—Exemplary Color Layer According to the Invention

An exemplary color layer formulation according to the invention is provided in Table 7.

TABLE 7

| Materials | wt % |
|---|---|
| Polypropyleneglycol (5) methacrylate | 23.41 |
| Tetrahydrofurfuryl methacrylate | 5.82 |
| Cellulose acetate butyrate | 17.84 |
| Urethane dimethacrylate | 2.00 |
| Bis-HEMA poly(caprolactone/pentaerythritol)/IPDI copolymer succinate | 23.26 |
| Bis-ethylhexyl poly(caprolactone/pentaerythritol)/IPDI copolymer | 5.83 |
| 37.5% Pyromellitic dianhydride glycerol dimethacrylate adduct in acetone | 0.50 |
| Butyl acetate | 16.17 |
| Butylated hydroxytoluene | 0.13 |
| 0.1% external violet 2 dye in hydroxypropylmethacrylate | 1.14 |
| Irgacure 819 | 0.45 |
| Ethyl (2,4,6-trimethylbenzoyl) phenylphosphinate | 1.35 |
| Isotridecylcarbamatotolylaminohexylurea | 0.20 |
| M5 Silica | 1.40 |
| Isooctyl/methoxy PEG-10 polysilsesquioxane (POSS) | 0.50 |

What is claimed is:

1. A nail coating formulation comprising a compound of formula (I):

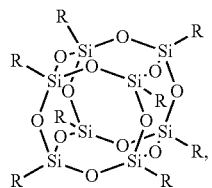

wherein at least one R group is a group comprising polyethylene glycol units and the R groups, other than the at least one R group, are alkyl groups.

2. The nail coating formulation of claim 1, wherein the formulation comprises about 0.1-10 wt % of the compound of formula (I).

3. The nail coating formulation of claim 1, wherein the formulation comprises a fatty alcohol methacrylate.

4. The nail coating formulation of claim 3, wherein the fatty alcohol methacrylate is stearyl methacrylate or cetyl methacrylate or a mixture thereof.

5. The nail coating formulation of claim 4, wherein the formulation comprises about 0.1-10 wt % fatty alcohol methacrylate.

6. The nail coating formulation of claim 1, wherein the formulation comprises a polyurethane.

7. The nail coating formulation of claim 6, wherein the polyurethane is selected from the group consisting of bis-HEMA poly(1,4-butanediol)/IPDI copolymer, bis-HEMA poly(caprolactone/neopentyl glycol)/IPDI copolymer, bis-HEMA poly(caprolactone/neopentyl glycol)/1,4-butanediol/IPDI copolymer, bis-ethylhexyl poly(caprolactone neopentyl glycol)/IPDI copolymer, bis-HEMA poly(caprolactone/pentaerythritol)/IPDI copolymer, bis-ethylhexyl poly(caprolactone/pentaerythritol)/IPDI copolymer, bis-HEMA poly(caprolactone/pentaerythritol)/IPDI copolymer succinate, or bis-ethylhexyl poly(caprolactone/pentaerythritol)/IPDI copolymer succinate, and mixtures thereof.

8. The nail coating formulation of claim 1, wherein the formulation comprises trimethylolpropane trimethacrylate.

9. The nail coating formulation of claim 8, wherein the formulation comprises about 0.1-10 wt % of trimethylolpropane trimethacrylate.

10. The nail coating formulation of claim 1, wherein the formulation comprises about 0.5 wt % of the compound of formula (I) and about 0.5 wt % of stearyl methacrylate.

11. The nail coating formulation of claim 1, wherein only one R group of the compound of formula (I) is a group comprising polyethylene glycol units.

12. The nail coating formulation of claim 11, wherein the alkyl groups of the compound of formula (I) have from 1 to 20 carbon atoms.

13. The nail coating formulation of claim 12, wherein the alkyl groups of the compound of formula (I) are —CH$_2$CH(CH$_3$)CH$_2$C(CH$_3$)$_3$ groups.

14. The nail coating formulation of claim 11, wherein the group of the compound of formula (I) comprising polyethylene glycol units has the formula —(CH$_2$)$_3$(OCH$_2$CH$_2$)$_m$OCH$_3$, wherein the average value of m ranges from 1 to 50.

15. The nail coating formulation of claim 1, wherein the compound of formula (I) is

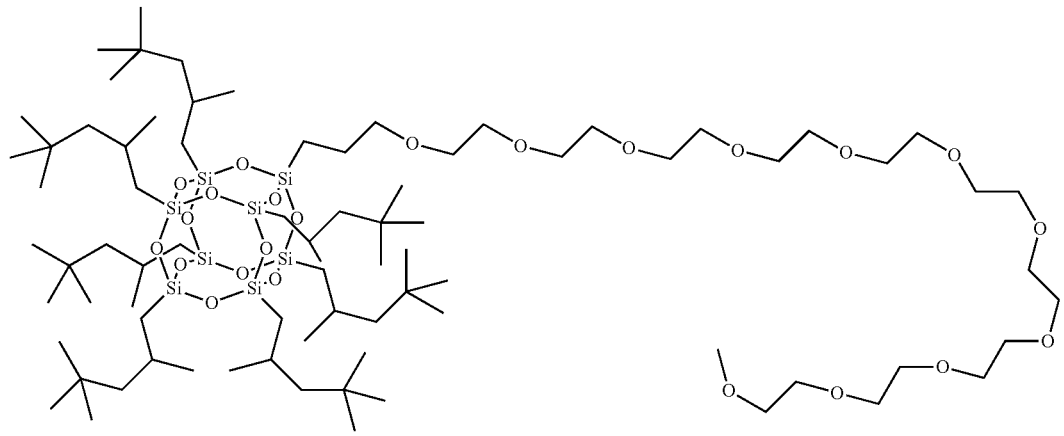

16. A method of coating a nail comprising applying the formulation of claim 1 to a nail surface.

17. The method of claim 16, wherein the formulation is applied directly to the nail surface.

18. The method of claim 16, wherein the formulation is applied onto a layer of another nail coating.

* * * * *